(12) United States Patent
Groszmann et al.

(10) Patent No.: US 8,067,726 B2
(45) Date of Patent: Nov. 29, 2011

(54) UNIVERSAL INSTRUMENT CALIBRATION SYSTEM AND METHOD OF USE

(75) Inventors: Daniel Eduardo Groszmann, Cambridge, MA (US); Jonathan Schiff, Andover, MA (US); Ella Zaslavsky, Marblehead, MA (US)

(73) Assignee: General Electric Company, Schenectady, NY (US)

( * ) Notice: Subject to any disclaimer, the term of this patent is extended or adjusted under 35 U.S.C. 154(b) by 1312 days.

(21) Appl. No.: 11/678,985

(22) Filed: Feb. 26, 2007

(65) Prior Publication Data

US 2008/0204000 A1  Aug. 28, 2008

(51) Int. Cl.
*G01D 18/00* (2006.01)
(52) U.S. Cl. .................................................. 250/252.1
(58) Field of Classification Search ............... 250/252.1; 324/202; 600/117
See application file for complete search history.

(56) References Cited

U.S. PATENT DOCUMENTS

| | | | |
|---|---|---|---|
| 4,800,877 A * | 1/1989 | Losch | 606/2 |
| 6,347,460 B1 * | 2/2002 | Forrer et al. | 33/626 |
| 6,511,418 B2 | 1/2003 | Shahidi | |
| 6,517,478 B2 * | 2/2003 | Khadem | 600/117 |
| 7,043,961 B2 * | 5/2006 | Pandey et al. | 73/1.81 |
| 7,153,297 B2 * | 12/2006 | Peterson | 606/1 |
| 2005/0096536 A1 * | 5/2005 | Peterson | 600/427 |
| 2006/0030771 A1 * | 2/2006 | Levine et al. | 600/424 |
| 2007/0142707 A1 * | 6/2007 | Wiklof et al. | 600/118 |
| 2008/0161679 A1 * | 7/2008 | von Jako et al. | 600/424 |

* cited by examiner

*Primary Examiner* — David Porta
*Assistant Examiner* — Marcus H Taningco
(74) *Attorney, Agent, or Firm* — McAndrews, Held & Malloy, Ltd.; William Baxter

(57) ABSTRACT

Certain embodiments of the present invention provide systems and methods for electromagnetic calibration of an instrument. Certain embodiments provide an electromagnetic instrument calibration system including electromagnetic receiver electronics for receiving electromagnetic field information from an electromagnetic transmitter. The system also includes a calibration mount configured to position the electromagnetic receiver electronics stationary with respect to the calibration mount for calibrating an instrument having an electromagnetic transmitter using the calibration mount and the electromagnetic receiver electronics. Certain embodiments provide a method for calibration of an instrument based on electromagnetic field information including providing a calibration mount accommodating a plurality of instruments in a known position and orientation and having electromagnetic calibration electronics positioned with respect to the calibration mount; receiving electromagnetic field information for an instrument with respect to a known position of the calibration mount and electromagnetic calibration electronics; and calibrating at least a portion of the instrument.

16 Claims, 11 Drawing Sheets

UNIVERSAL INSTRUMENT CALIBRATION SYSTEM AND METHOD OF USE

BACKGROUND OF THE INVENTION

The present invention generally relates to instrument calibration. In particular, the present invention relates to a universal calibration device for electromagnetic calibration of clinical instruments.

In medical and surgical imaging, such as intraoperative or perioperative imaging, images are formed of a region of a patient's body. The images are used to aid in an ongoing procedure with an instrument (e.g., a surgical tool, imaging tool, diagnostic tool, etc.) applied to the patient and tracked in relation to a reference coordinate system formed from the images. Image-guided surgery is of a special utility in surgical procedures such as brain surgery and arthroscopic procedures on the knee, wrist, shoulder or spine, as well as certain types of angiography, cardiac procedures, interventional radiology and biopsies in which x-ray images may be taken to display, correct the position of, or otherwise navigate a tool or instrument involved in the procedure.

Medical navigation systems track precise locations of surgical instruments in relation to multidimensional images of a patient's anatomy. Additionally, medical navigation systems use visualization tools to provide the surgeon with co-registered views of these surgical instruments with the patient's anatomy. To help ensure tracking accuracy, instruments should be calibrated with respect to the medical navigation system.

Computer-assisted methods now provide real-time navigation during surgical procedures, including analysis and inspection of three-dimensional (3D) diagnostic images from magnetic resonance (MR) and computed tomography (CT) data. Instrumentation has also undergone rapid development, providing instrumentation for use in small body cavities and minimally invasive procedures. The combination of instruments and computer-generated 3D images may help to overlay instrument tracking information with volumetrically reconstructed patient images in a surgical field. Thus, surgeons can look beyond visible surfaces and provide "on-the-fly" 3D and two-dimensional (2D) information for planning and navigational purposes.

Tracking systems may be ultrasound, optical, inertial position, and/or electromagnetic tracking systems, for example. Electromagnetic tracking systems may employ coils as receivers and transmitters. Electromagnetic tracking systems may be configured in sets of three transmitter coils and three receiver coils, such as an industry-standard coil architecture (ISCA) configuration. Electromagnetic tracking systems may also be configured with a single transmitter coil used with an array of receiver coils or an array of transmitter coils with a single receiver coil, for example. Magnetic fields generated by the transmitter coil(s) may be detected by the receiver coil(s). For obtained parameter measurements, position and orientation information may be determined for the transmitter and/or receiver coil(s).

Due to many parameters involved in typical instrument function, however, small errors in settings of the instrument may have relatively large and cumulative effects such as contributing to a discrepancy between image data position and tracked position. Thus, there is a need for more precise calibration of an instrument and accuracy testing of the calibrated instrument.

BRIEF SUMMARY OF THE INVENTION

Certain embodiments of the present invention provide systems and methods for electromagnetic calibration of an instrument.

Certain embodiments provide an electromagnetic instrument calibration system. The system includes electromagnetic receiver electronics for receiving electromagnetic field information from an electromagnetic transmitter. The system also includes a calibration mount configured to position the electromagnetic receiver electronics stationary with respect to the calibration mount for calibrating an instrument having an electromagnetic transmitter using the calibration mount and the electromagnetic receiver electronics.

Certain embodiments provide an electromagnetic instrument calibration system. The system includes electromagnetic calibration electronics for generating position and orientation information based on electromagnetic field information. The system also includes a calibration mount configured to position the electromagnetic calibration electronics stationary with respect to the calibration mount for calibrating an instrument using the calibration mount and the electromagnetic calibration electronics.

Certain embodiments provide a method for calibration of an instrument based on electromagnetic field information. The method includes providing a calibration mount having a plurality of positioning mechanisms to accommodate a plurality of instruments in a known position and orientation for calibration and the calibration mount having electromagnetic calibration electronics operably positioned in a stationary position with respect to the calibration mount. The method also includes receiving electromagnetic field information for an instrument with respect to a known position of the calibration mount and electromagnetic calibration electronics. The method further includes calibrating at least a portion of the instrument with respect to at least one of an electromagnetic transmitter and an electromagnetic receiver positioned on or in the instrument using the electromagnetic field information.

Figure 1:
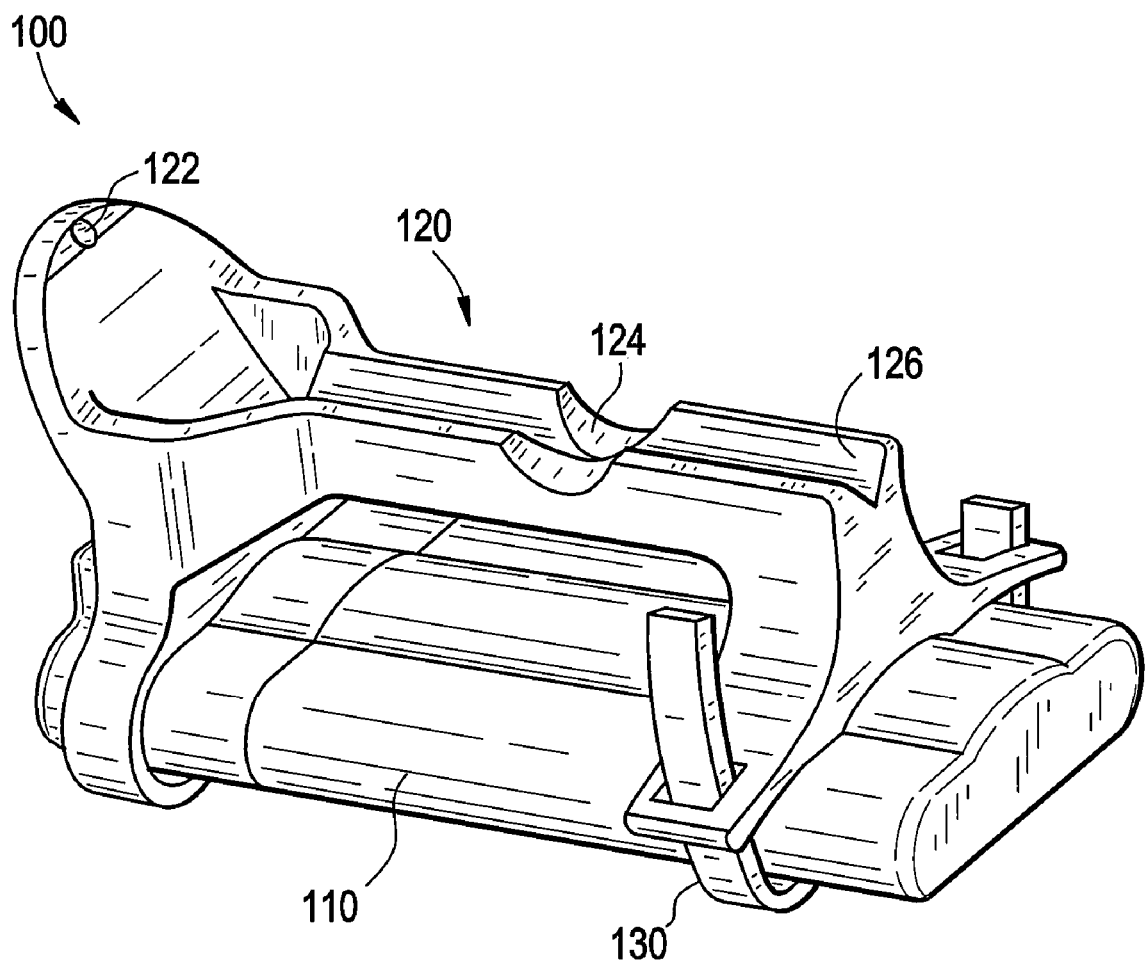
FIG. 1 illustrates a calibration device in accordance with an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments provide a calibration device including a single transmitter and receiver array. Certain embodiments enable electromagnetic (EM) surgical navigation on computed tomography (CT) and/or magnetic resonance (MR) imaging. Certain embodiments enable image-guided augmented endoscopy with CT and MR images.

Certain embodiments provide a universal calibration device with calibration mount and receiver array. In certain embodiments, the receiver array may be covered with a sterile covering, such as a removable bag or sleeve, because electronics in the array cannot be autoclaved. However, the mount may be autoclaved and/or otherwise sterilized, for example. The calibration device may thus be used to calibrate sterile instruments in an operating or other sterile environment, for example.

In certain embodiments, a bag or other type of sleeve is placed over the electronics. The sleeve is selected so as to not interfere with EM signal information but to protect the electronics and/or help preserve a sterile environment. The electronics are then inserted or otherwise connected to or combined with the calibration device in a repeatable location that does not tear the bag, for example. The electronics may be inserted in the same location without the bag, for example.

An EM array or other electronics is placed on a calibration device so that EM equipment may be calibrated with respect to the device regardless of location and/or situation. For example, EM equipment may be calibrated without having to be on or near a patient. The tracking of the EM equipment or instruments on the patient may be accomplished by a separate EM array on, below, or near the patient, for example. The calibration device has one or more known points, for use in instrument calibration. In certain embodiments, an associated tracking and/or computing system knows that a user is trying to calibrate an instrument enabled for EM tracking when the instrument is brought near the array. The calibrated instrument may be used in combination with image data, for example, such as MR imaging data, CT imaging data, etc.

In certain embodiments, the calibration device is made of a sterilizable material. In certain embodiments, the calibration device may be sterilized before a procedure, for example. The calibration device has bottom portion for attachment of the electronics and a top cradle or mount for instrument, such as probe, catheter, endoscope, rod, etc., calibration. The calibration device also has a calibrating dimple for calibration of current and future instruments.

In certain embodiments, a rechargeable receiver array may be implemented as an electronic box or other unit. The electronic box may have a cable and/or other communication port attached to an open end, for example. The electronics may be wiped clean and bagged into a sterile clear polyethylene sleeve for insertion into the calibration mount, for example. In certain embodiments, the sleeve may be up to 4 feet long and covering the connecting cable, for example.

In certain embodiments, a front of the electronics array is tapered. Tapering allows for a snug positioning against a bracket or holder on the calibration mount. In certain embodiments, an opposite end of the electronics also has a taper so that, when the holder snaps in place, the holder moves the electronics up against the calibration device bracket. In certain embodiments, the electronics box has one or more momentary switches (e.g., on the front of the electronics).

Figure 2:
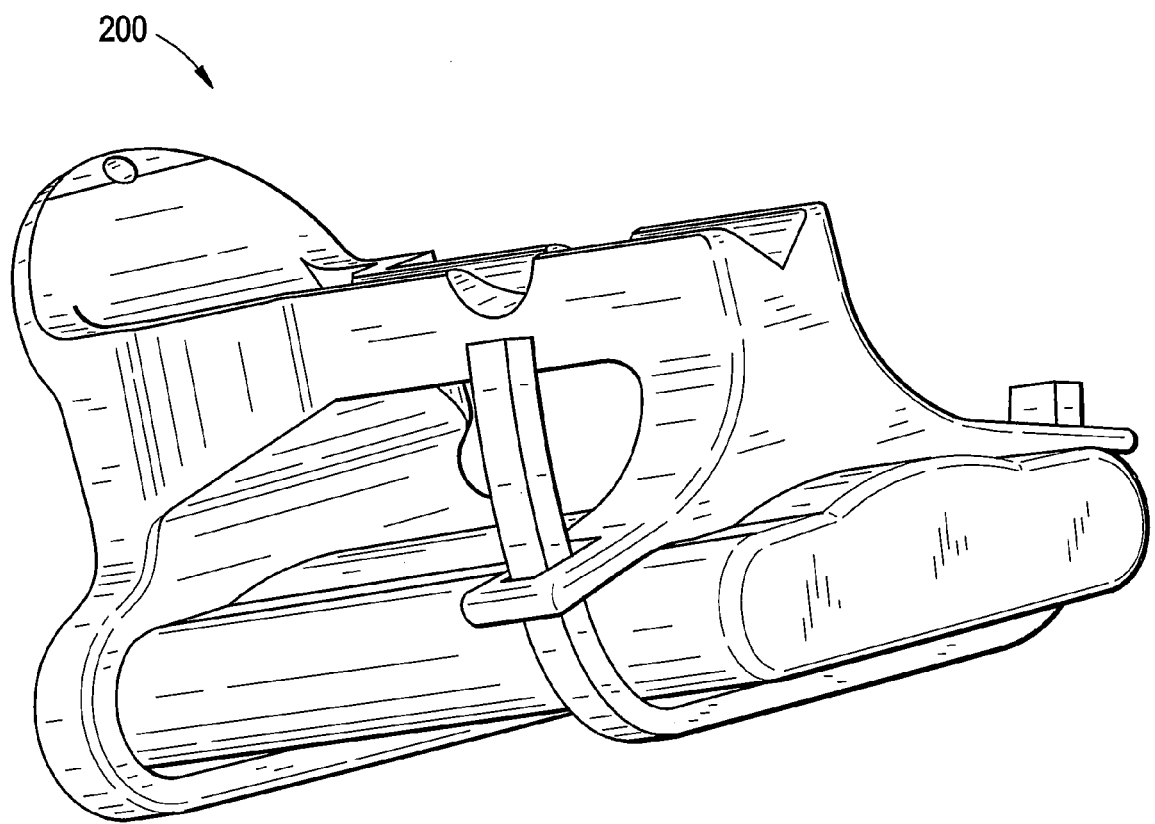
FIG. 2 illustrates another view of a calibration device with receiver electronics positioned with respect to a calibration mount in accordance with an embodiment of the present invention.
Figure 3:
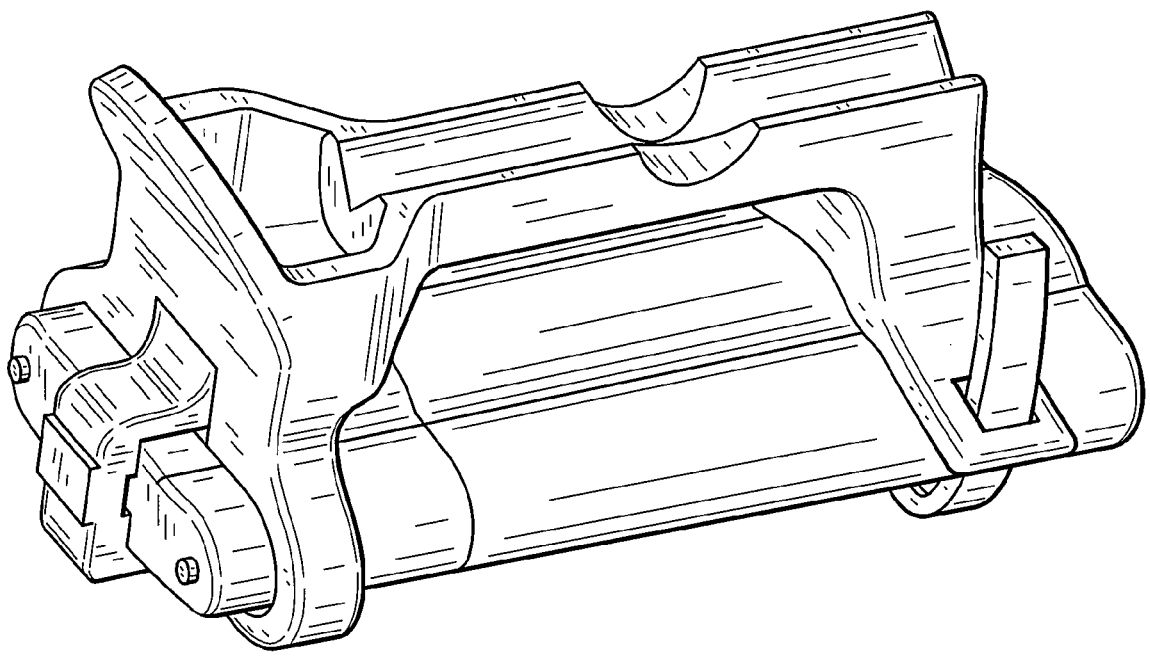
FIG. 3 depicts a top view of a calibration device having a calibration mount and receiver electronics in accordance with an embodiment of the present invention.
Figure 4:
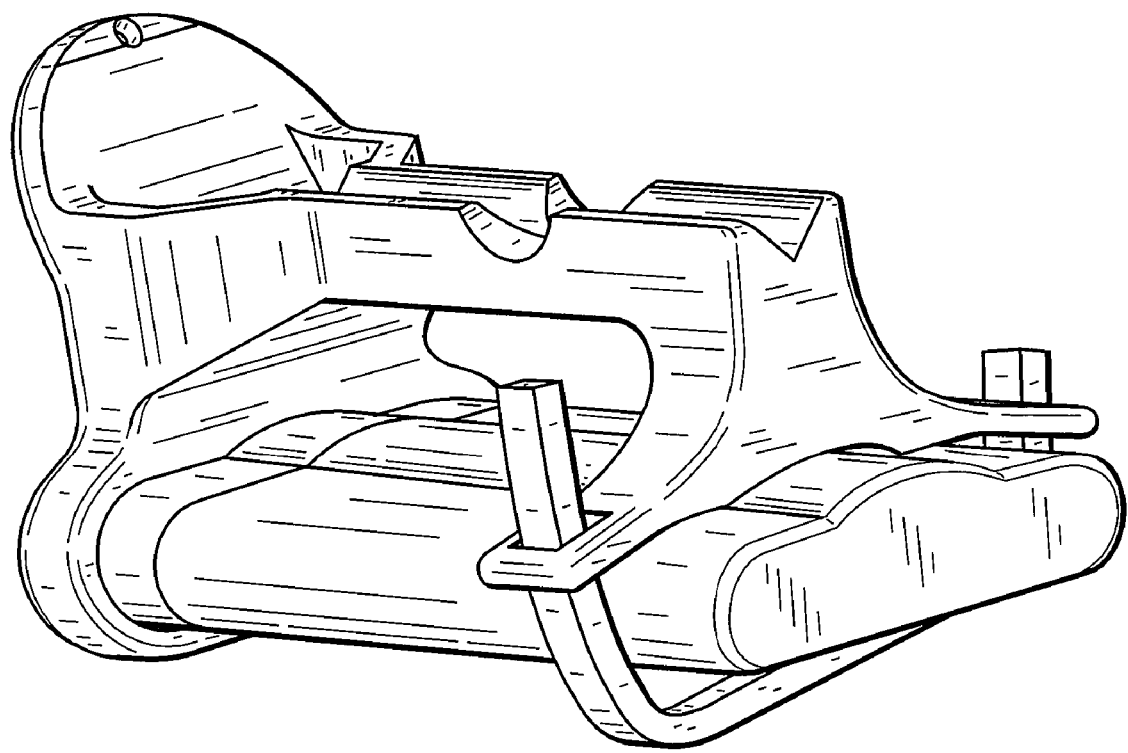
FIG. 4 illustrates a front view of a calibration device with a receiver electronics holder in an open position in accordance with an embodiment of the present invention.
Figure 5:
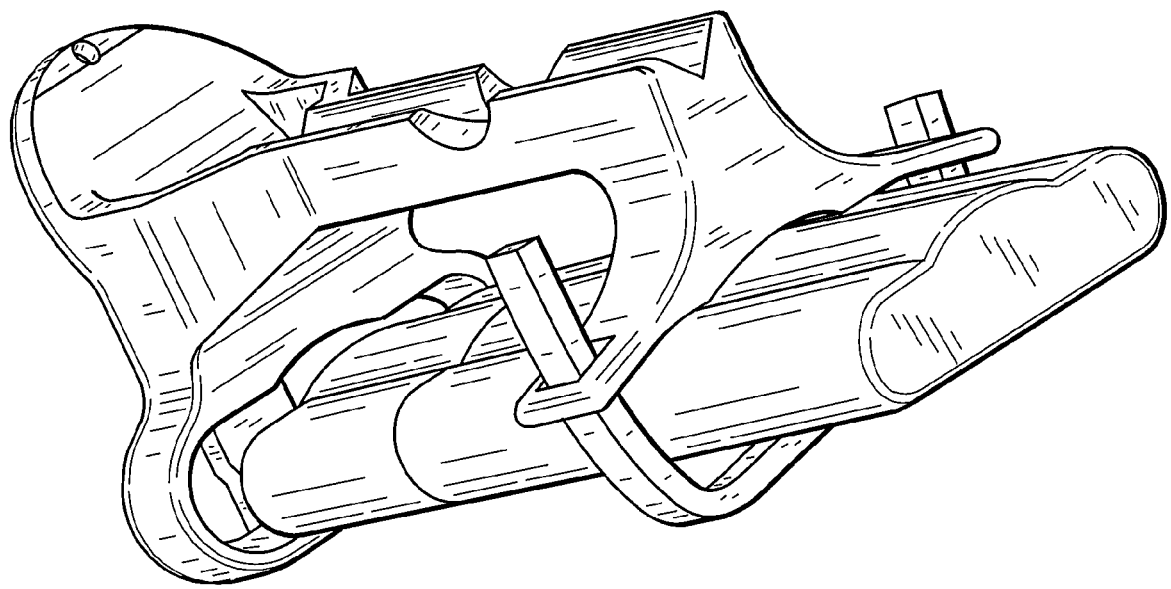
FIG. 5 depicts a side view of a calibration device with a receiver electronics holder in an open position in accordance with an embodiment of the present invention.
Figure 6:
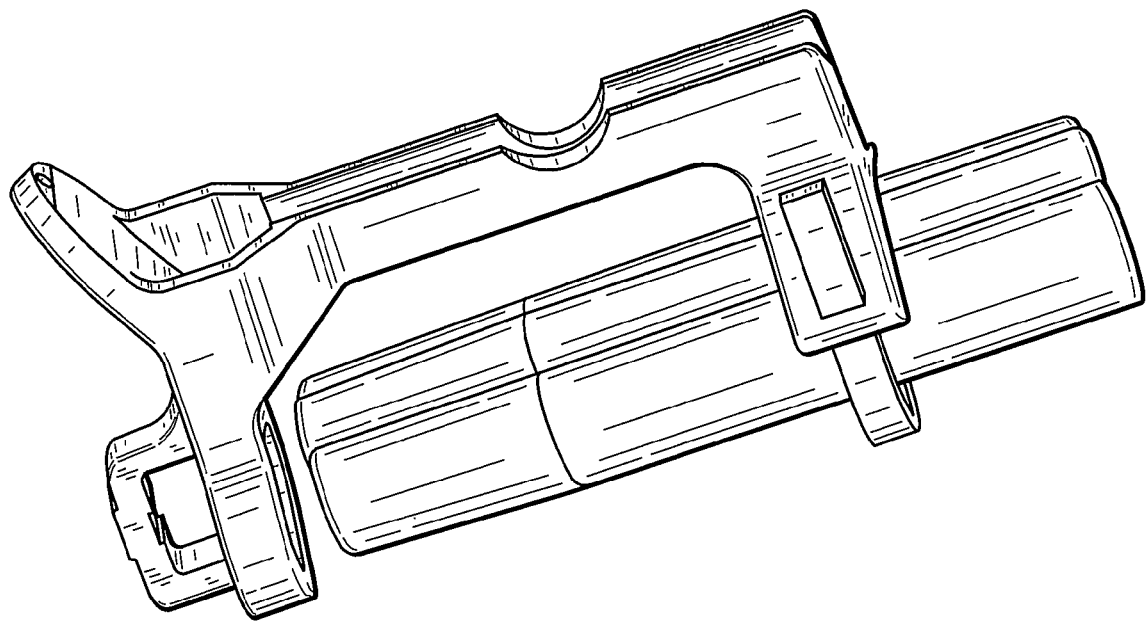
FIG. 6 depicts a side view of a calibration device with a receiver electronics in an undocked position in accordance with an embodiment of the present invention.

As will be discussed further below, FIG. 1 illustrates a calibration device in accordance with an embodiment of the present invention. FIG. 2 illustrates another view of a calibration device with receiver electronics positioned with respect to the calibration mount in accordance with an embodiment of the present invention. FIG. 3 depicts a top view of a calibration device having a calibration mount and receiver electronics in accordance with an embodiment of the present invention. FIG. 4 illustrates a front view of a calibration device with a receiver electronics holder in an open position in accordance with an embodiment of the present invention. FIG. 5 depicts a side view of a calibration device with a receiver electronics holder in an open position in accordance with an embodiment of the present invention. FIG. 6 depicts a side view of a calibration device with receiver electronics in an undocked position in accordance with an embodiment of the present invention.

Figure 7:
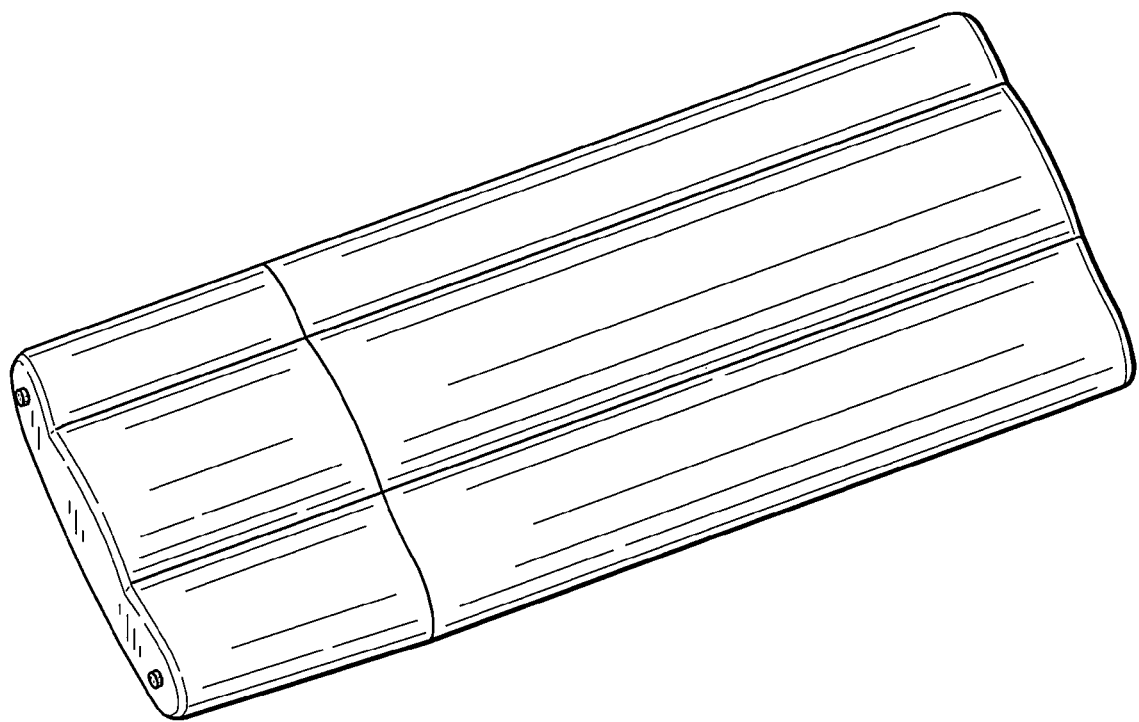
FIG. 7 depicts a top view of an electronics box containing a receiver array in accordance with an embodiment of the present invention.
Figure 8:
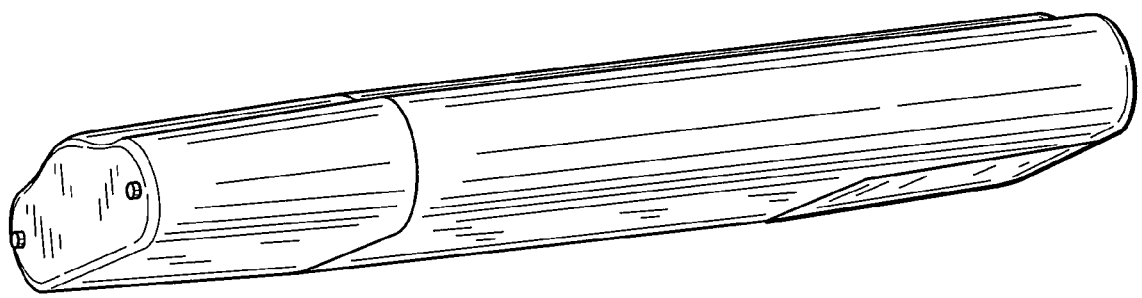
FIG. 8 shows a side view of an electronics box containing a receiver array in accordance with an embodiment of the present invention.
Figure 9:
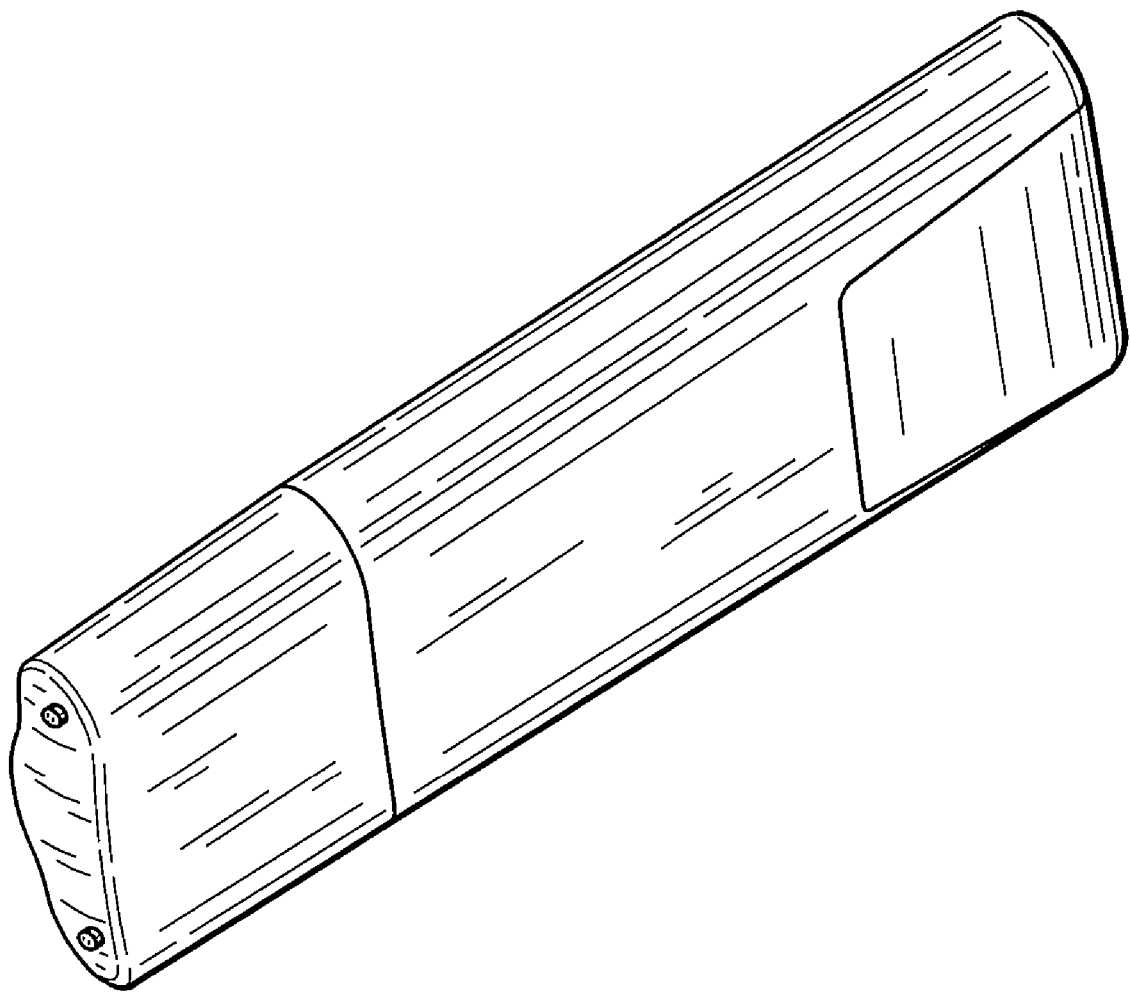
FIG. 9 illustrates a bottom view of an electronics box containing a receiver array in accordance with an embodiment of the present invention.

FIGS. 7-9 depict views of a receiver electronics unit in accordance with certain embodiments of the present invention. FIG. 7 depicts a top view of an electronics box containing a receiver array in accordance with an embodiment of the present invention. FIG. 8 shows a side view of an electronics box containing a receiver array in accordance with an embodiment of the present invention. FIG. 9 illustrates a bottom view of an electronics box containing a receiver array in accordance with an embodiment of the present invention.

A calibration procedure involves, in part, establishing a relationship between a tracking assembly attached to and/or integrated with an instrument and a body and/or tip of the instrument, for example. For purposes of illustration only, the tracking assembly may be a transmitter and a calibration device may include a receiver, but the tracking assembly may also be a receiver capable of communicating with a transmitter in the calibration device.

During use of an instrument, a tracking system tracks the position and orientation of the tracking assembly on/in the instrument. Therefore, a relative position between the tracking assembly and the body and/or tip of the instrument may be determined before, during and/or after use of the instrument. Calibration of the instrument with respect to the tracking assembly may help in acquiring, processing and/or displaying 2D and/or 3D image(s) in view of tracking information.

FIG. 1 illustrates a calibration device 100 used for instrument calibration in accordance with an embodiment of the present invention. The calibration device 100 includes receiver electronics 110, a calibration mount 120, and an electronics holder 130. The calibration mount 120 includes a pivot point or dimple 122 for calibration of an instrument tip, for example. The calibration mount 120 also includes one or more channels 124, 126 for instrument body calibration, for example.

The calibration mount 120 may be used with the receiver electronics 110 to calibrate an instrument (not shown). For example, a tip of an instrument, such as a probe, may be placed in the dimple 122 and measured at one or more orientations. As another example, an instrument, such as a catheter or endoscope, may be laid and/or otherwise positioned in one or more of the channels 124, 126 of the calibration mount 120 for calibration measurement of its angle or trajectory.

In certain embodiments, the receiver electronics 110 are affixed and/or integrated with the calibration mount 120. For example, as illustrated in FIG. 1, the receiver electronics 110 may be positioned with respect to the calibration mount 120 using the holder 130. The holder 130 may snap, clip and/or otherwise position the receiver electronics 110 into the calibration mount 120, for example. Using the holder 130, the receiver electronics 110 may be fixed in a known position with respect to the calibration mount 120.

The receiver electronics 110 and calibration mount 120 may be used with an instrument transmitter and/or other tracking assembly to provide information relating to position, orientation and/or movement of an instrument and/or other device with six degrees of freedom, for example. The receiver electronics 110 and calibration mount 120 may be used with an instrument transmitter and/or other tracking assembly to determine three-dimensional coordinates of the instrument, as well as angle and/or other orientation of the instrument, for example.

The system 100 may include and/or be used with software to process signals from the receiver electronics 110 to generate data indicating the location and orientation of the instrument with respect to the known configuration of the receiver electronics 110 and the calibration mount 120. In certain embodiments, location and orientation data may be generated periodically, upon request and/or on a continuous (or substantially continuous) basis.

The calibration mount 120 provides multiple ways for instruments to be calibrated, thus accommodating a variety of instruments for calibration. Channels 124, 126 of varying width and/or length accommodate a variety of instruments, for example. The dimple 122 accommodates a variety of instrument tips, for example.

For example, one or more channels 124, 126 and/or dimples 122 are located in known and/or pre-calibrated positions on the calibration mount 120. An instrument may be placed, slid and/or otherwise positioned with respect to one of more of the channels 124, 126, dimple 122, etc. Once positioned, at least one reference point (e.g., a tip) on the instrument is at a known position with respect to the channel 124, 126 and/or dimple 122 on the calibration mount 120 (and thus with respect to the electronics 110). In certain embodiments, the channel(s) 124, 126 and/or dimple 122 may be of fixed diameter. Alternatively and/or in addition, one or more of the channel(s) 124, 126 and/or dimple 122 may be of a variable or adjustable (manually and/or automatically) diameter, for example.

During calibration, the instrument positioned in/on the calibration mount 120 is tracked using the receiver electronics 110. Data is then transmitted from the receiver electronics 110 to a computing device and/or other tracking electronics to calibration a position and/or orientation of the instrument in a reference coordinate space. Data may be transmitted from the receiver electronics 110 using wired (e.g., a cable) and/or wireless data communication, for example. Data regarding the instrument and/or its components (e.g., tip, body, transmitter, etc.) may be stored for further use in surgery or other procedure, for example.

Figure 10:
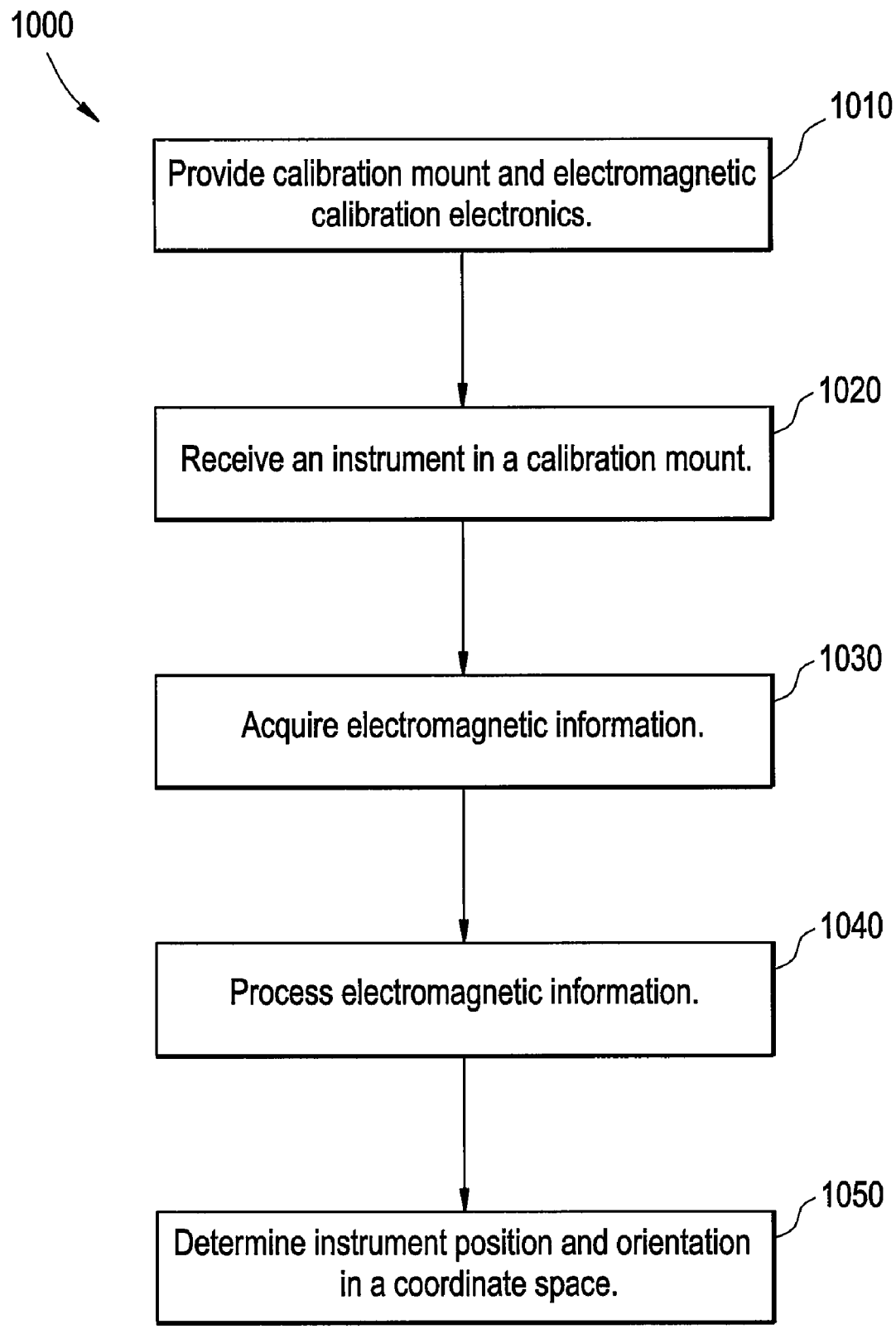
FIG. 10 illustrates a flow diagram for a method for instrument calibration used in accordance with an embodiment of the present invention.

FIG. 10 illustrates a flow diagram for a method 1000 for instrument calibration based on electromagnetic field information used in accordance with an embodiment of the present invention. At step 1010, a calibration mount and electromagnetic calibration electronics are provided. At step 1020, an instrument is received in a calibration mount. For example, an instrument is received in a dimple 122 or channel 124, 126 of a calibration mount 120.

At step 1030, electromagnetic information is acquired. For example, electromagnetic field(s) generated at a transmitter and received at a receiver are acquired. At step 1040, EM information is processed. At step 1050, position and orientation of the instrument are determined in a coordinate space. Through determination of position and orientation, at least a portion of the instrument is calibrated with respect to an electromagnetic transmitter and/or receiver positioned on or in the instrument.

Figure 11:
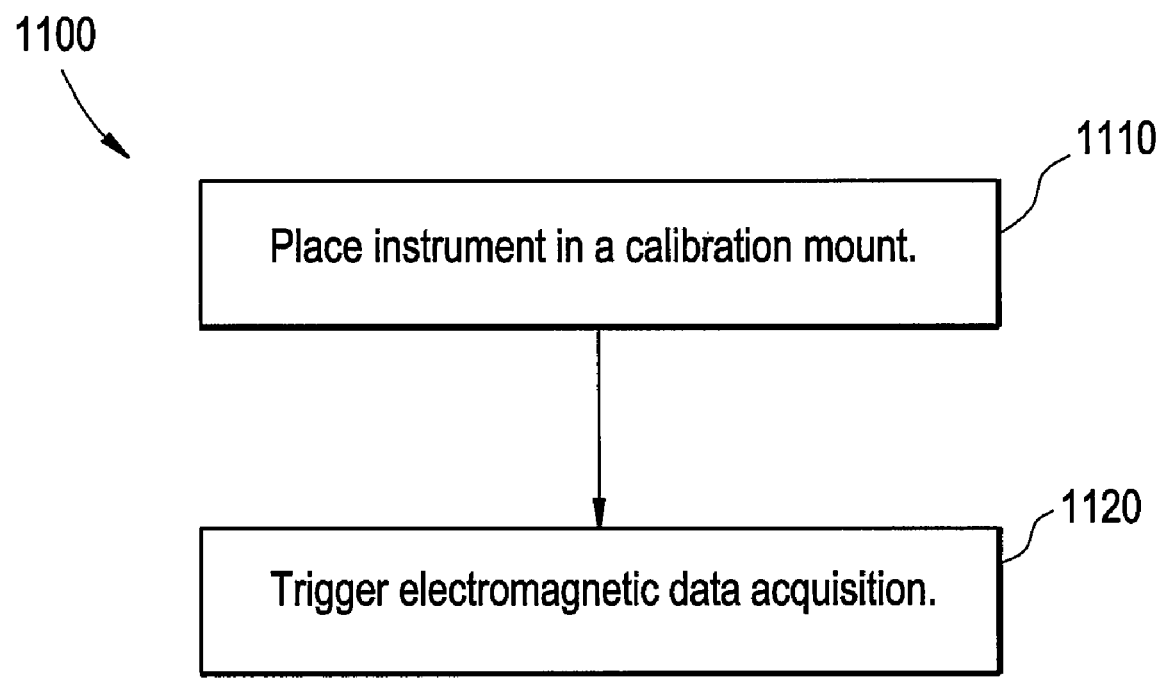
FIG. 11 illustrates a flow diagram for a method for user calibration of an instrument in accordance with an embodiment of the present invention.

FIG. 11 illustrates a flow diagram for a method 1100 for user calibration of an instrument in accordance with an embodiment of the present invention. At step 1110, an instrument is placed in a calibration mount. For example, an instrument is laid in a channel 124 in the calibration mount 120. At step 1120, electromagnetic data acquisition is triggered. For example, a user may select or execute a command to acquire electromagnetic field information related to the instrument in the calibration mount. In certain embodiments, data acquisition is automatically triggered when the instrument is positioned with respect to the calibration mount for a certain period of time. In certain embodiments, EM data acquisition may be acquired more that once to help produce a more accurate and reliable calibration of an instrument. Calibration information may then be used in an image-guided procedure that allows 2D and/or 3D image reconstruction in relation to the instrument.

In certain embodiments, electromagnetic calibration electronics may be a printed circuit board, for example. Certain embodiments may include an electromagnetic sensor comprising a printed circuit board receiver array including a plurality of coils and coil pairs and electronics for digitizing magnetic field measurements detected in the printed circuit board receiver array, for example. The magnetic field measurements can be used to calculate the position and orientation of the electromagnetic field generator, such as the instrument with a transmitter, according to any suitable method or system. After the magnetic field measurements are digitized using electronics on the electromagnetic sensor, the digitized signals may be transmitted to a navigation interface, for example. A medical navigation system may be configured to calculate a location of the instrument based on the received digitized signals.

In certain embodiments, many different types of devices for use in different procedures may be calibrated and/or tracked. Depending on the procedure, the device may be a surgical instrument (e.g., an imaging catheter, a diagnostic catheter, a therapeutic catheter, a guidewire, a debrider, an aspirator, a handle, a guide, etc.), a surgical implant (e.g., an artificial disk, a bone screw, a shunt, a pedicle screw, a plate, an intramedullary rod, etc.), or some other device. Depending on the context of the usage of the medical navigation system, any number of suitable devices may be used.

In certain embodiments, one or more of the electronics and tracking systems may be implemented as any one or combination of a collection of modules, dedicated hardware boards, digital signal processors, field programmable gate arrays, and processors, for example. Alternatively, components may be implemented using an off-the-shelf computer with a single processor or multiple processors, with the functional operations distributed between the processors. As an example, it may be desirable to have a dedicated processor for position and orientation calculations as well as a dedicated processor for visualization operations. As a further option, components may be implemented using a hybrid configuration in which certain modular functions are performed using dedicated hardware, while the remaining modular functions are performed using an off-the-shelf computer. In certain embodiments, operations may be controlled by a system controller.

In certain embodiments, a navigation interface receives signals from the receiver electronics representing magnetic field information detected by an electromagnetic sensor. A tracker module or similar system may be used to calculate position and orientation information based on the received signals. This position and orientation information provides a location of an instrument.

Position and orientation information may be used to register the location of the instrument to acquired patient data, for example. The acquired patient data may include computed tomography data, magnetic resonance data, positron emission tomography data, ultrasound data, X-ray data, or any other suitable data, as well as any combinations thereof. Information, such as position and orientation information, registration information and/or patient data, may be stored and/or temporary used, for example. In certain embodiments, an instrument registration is used with patient data to generate image data suitable to visualize the patient image data and a representation of the instrument, for example.

Several embodiments are described above with reference to drawings. These drawings illustrate certain details of specific embodiments that implement the systems and methods and programs of the present invention. However, describing the invention with drawings should not be construed as imposing on the invention any limitations associated with features shown in the drawings. The present invention contemplates methods, systems and program products on any machine-readable media for accomplishing its operations. As noted above, the embodiments of the present invention may be implemented using an existing computer processor, or by a special purpose computer processor incorporated for this or another purpose or by a hardwired system.

As noted above, embodiments within the scope of the present invention include program products comprising machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Embodiments of the invention are described in the general context of method steps which may be implemented in one embodiment by a program product including machine-executable instructions, such as program code, for example in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules and other data for the computer.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated.

Those skilled in the art will appreciate that the embodiments disclosed herein may be applied to the formation of any medical navigation system. Certain features of the embodiments of the claimed subject matter have been illustrated as described herein, however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

The invention claimed is:

1. An electromagnetic instrument calibration system, said system comprising:
   electromagnetic receiver electronics for receiving electromagnetic field information from an electromagnetic transmitter of a tracking assembly; and
   a calibration mount affixed to said electromagnetic receiver electronics so that a position of said electromagnetic receiver electronics is stationary with respect to said calibration mount, said electromagnetic instrument calibration system configured to calibrate an instrument having said electromagnetic transmitter with respect to a medical navigation system, said electromagnetic calibration system configured to calibrate said instrument received at said calibration mount using said calibration mount and said electromagnetic receiver electronics.

2. The system of claim 1, wherein said calibration mount comprises a dimple for positioning said instrument with respect to said calibration mount and said electromagnetic receiver electronics to calculate position and orientation of the instrument and calibrate a tip of said instrument.

3. The system of claim 1, wherein said calibration mount comprises one or more channels for positioning said instrument with respect to said calibration mount and said electromagnetic receiver electronics to calculate position and orientation of the instrument and calibrate an angle of said instrument.

4. The system of claim 1, further comprising a sleeve for protecting said electromagnetic receiver electronics.

5. The system of claim 1, wherein said calibration mount comprises an autoclavable material.

6. The system of claim 1, wherein said calibration mount further comprises a holder for positioning said electromagnetic receiver electronics stationary with respect to said calibration mount by affixing said electromagnetic receiver electronics to said calibration mount.

7. The system of claim 6, wherein said holder comprises at least one of a clip and a snap.

8. The system of claim 1, wherein said electromagnetic receiver electronics transmits said received electromagnetic field information to an external system for calibrating said instrument with respect to a reference coordinate system.

9. A method for calibration of an instrument, said method comprising:
   receiving an instrument comprising an electromagnetic transmitter of a tracking assembly at a calibration mount affixed to electromagnetic receiver electronics so that the position of said electromagnetic receiver electronics is stationary with respect to said calibration mount;
   receiving, at said electromagnetic receiver electronics, electromagnetic field information from said electromagnetic transmitter of said instrument; and
   calibrating said instrument received at said calibration mount with respect to a medical navigation system using said calibration mount and said electromagnetic receiver electronics.

10. The method of claim 9, wherein said receiving said instrument comprises using a dimple at said calibration mount for positioning said instrument with respect to said calibration mount and said electromagnetic receiver electronics to calculate position and orientation of the instrument and calibrate a tip of said instrument.

11. The method of claim 9, wherein said receiving said instrument comprises using one or more channels for positioning said instrument with respect to said calibration mount and said electromagnetic receiver electronics to calculate position and orientation of the instrument and calibrate an angle of said instrument.

12. The method of claim 9, comprising protecting said electromagnetic receiver electronics with a sleeve.

13. The method of claim 9, wherein said calibration mount comprises an autoclavable material.

14. The method of claim 9, comprising affixing said electromagnetic receiver electronics to said calibration mount using a holder for positioning said electromagnetic receiver electronics stationary with respect to said calibration mount.

15. The method of claim 14, wherein said holder comprises at least one of a clip and a snap.

16. The method of claim 9, comprising transmitting said received electromagnetic field information from said electromagnetic receiver electronics to an external system for calibrating said instrument with respect to a reference coordinate system.

* * * * *